US007695721B1

(12) United States Patent
Franks et al.

(10) Patent No.: US 7,695,721 B1
(45) Date of Patent: Apr. 13, 2010

(54) GONADOTROPHINS IN THE TREATMENT ANOVULATORY WOMEN

(75) Inventors: Stephen Franks, London (GB); Stephen Hillier, Edinburgh (GB)

(73) Assignee: Merck Serono S.A., Coinsins, Vaud (CH)

( * ) Notice: Subject to any disclaimer, the term of this patent is extended or adjusted under 35 U.S.C. 154(b) by 0 days.

(21) Appl. No.: 09/959,799

(22) PCT Filed: May 5, 2000

(86) PCT No.: PCT/GB00/01745

§ 371 (c)(1),
(2), (4) Date: Feb. 28, 2002

(87) PCT Pub. No.: WO00/67778

PCT Pub. Date: Nov. 16, 2000

(30) Foreign Application Priority Data

May 7, 1999 (EP) ................... 99303574

(51) Int. Cl.
    A61K 38/24    (2006.01)
    A61K 38/16    (2006.01)
    A61K 39/00    (2006.01)
    C07K 5/00     (2006.01)
(52) U.S. Cl. .............. 424/198.1; 530/398; 530/399
(58) Field of Classification Search .............. 514/2;
    424/85.1; 530/350, 351, 397, 399
    See application file for complete search history.

(56) References Cited

U.S. PATENT DOCUMENTS

| 4,845,077 | A | * | 7/1989 | Hodgen ......................... 514/2 |
| 4,959,354 | A | * | 9/1990 | Barbetti ....................... 514/21 |
| 5,162,306 | A | * | 11/1992 | Donaldson .................... 514/12 |
| 5,610,138 | A | * | 3/1997 | Jacobs ......................... 514/12 |
| 6,660,717 | B1 | * | 12/2003 | Rose et al. ..................... 514/2 |

FOREIGN PATENT DOCUMENTS

| EP | 0193277 A2 | 9/1986 |
| WO | WO 93/13799 | 7/1993 |

OTHER PUBLICATIONS

Tapanainen et al. (1993), Induction of Ovarian Follicle Luteinization by Recombinant Follicle-Stimulating Hormone, Endocrinology 133(6): 2875-2880.*
D'Alessandro et al. (1997), Some effects of adding p-LH in defined amounts to purified p-FSH to modify FSH/LH ratios during the superovulatory treatment of anestrous ewes, Animal Reproduction Science 47: 91-98.*
Breckwoldt et al., Fertility and Sterility, 1971, vol. 22, No. 7, pp. 451-455.*
Kistner, Fertility and Sterility, 1976, vol. 27, No. 1, pp. 72-82. (Abstract).*
Dickey et al., Human Reproduction, 1993, vol. 8, No. 1, pp. 56-59.*
The European Recombinant Human-LH Study Group, J. Clin. Endocrinol. Metab., 1998, vol. 83:1507-1514.*
Thompson et al., Fertility and Sterility, 1995, vol. 63, No. 2, pp. 273-276.*
Gonen et al., J., Clin. Endocrinol. Metab., 1990, 71(4):918-922, abstract.*
Sullivan et al., J. Clin. Endocrinol. Metab., Jan. 1999, 84(1):228-232.*
Loumaye et al., in: Treatment with GnRH Analogs: Controversies and Perspectives, edit. M. Filicori and C. Flamigni, published 1996, pp. 201-209.*
Baird et al., In: Ovulation Induction: Update '98: The Proceedings of the 2nd World Conference on Ovulation Induction: Bologna, Italy; Sep. 12-13, 1997; eds: Filicori and Flamigni; pp. 159-164.*
Farhi et al., Hum. Reprod., 1996, vol. 11(2):429-434.*
XP-002135914—Recombinant human luteinising hormone: an effective new gonadotropin preparation, *The Lancet*, 344:334-335 (1994).
Sullivan et al., Ovarian response in women to recombinant follicle-stimulating hormone and luteinizing hormone (LH): a role for LH in the final stages of follicular maturation, *Journal of Clinical Endocrinology and Metabolism*, 84:(1)228-232 (1999).
Hillier, Review—Current concepts of the roles of follicle stimulating hormone and luteinizing hormone in folliculogenesis, *Human Reproduction*, 9(2):188-191 (1994).
The European recombinant humna LH study group, Recombinant human luteinizing hormone (LH) to support recombinant human follicle-stimulating hormone (FSH)-induced follicular development in LH- and FSH-deficient anovulatory women: a dose-finding study, *Journal of Clinical Endocrinology and Metabolism*, 83(5)1507-1514 (1998).
World Health Organization, Agents Stimulating Gonadal Function in Human, WHO Technical Report Series No. 514 (1973).
Hillier, The New Frontier on Ovulation Induction, edited by H.S. Jacobs, The Parthenon Publishing Group, pp. 39-47 (1993).
Loumaye et al., Clinical Evidence for an LH "ceiling" effect induced by administration of recombinant human LH during the late follicular phase of stimulated cycles in World Health Organization type I and type II anovulation, Human Reproduction, 18(2):314-422 (2003).
Platteau et al., Similar ovulation rates, but different follicular development with highly purified menotrophin compared with recombinant FSH in WHO group II anovulatory infertility: a randomized controlled study, Human Reproduction Advance Access, pp. 1-7 (Mar. 2009).

(Continued)

*Primary Examiner*—Gary B Nickol
*Assistant Examiner*—Xiaozhen Xie
(74) *Attorney, Agent, or Firm*—Browdy and Neimark, PLLC

(57) ABSTRACT

The present invention relates to the use of gonadotrophins in the induction of folliculogenesis in anovulatory women. In particular, if relates to the use of LH (or an equivalent dosage of hCG) in the production of a medicament for inducing folliculogenesis in anovulatory women at a specified daily doses. In certain embodiments. LH may be used in conjunction with FSH.

2 Claims, 2 Drawing Sheets

OTHER PUBLICATIONS

Expert Opinion of Dr. Peter Platteau filed Nov. 20, 2008, regarding opposition in EP1176976B1.

Zeleznik and Sullivan, The Role of LH on Folliculogenesis and Uvulation Induction, Monduzzi Editione 1999, Proceedings of the workshop of ovulation induction, bologna, pp. 1-19 (Oct. 30 and 31, 1998).

Zelinski-Wooten et al., The Role of LH in Folliculogenesis and Uvulation Induction, Monduzzi Editione 1999, Proceedings of the Workshop of ovulation induction, bologna, pp. 21-36 (Oct. 30 and 31, 1998).

Gougeon, Human in vitro Fertilization, INSERM Symposium No. 24, Elsevier Science Publishers B. V., pp. 3-15 (1985).

Prof. Dr. Johan Smitz; Free University of Brussels, Expert Declaration (Aug. 2009).

Lunenfeld, B., Stimulations de l'ovulation: une nouvelle approche basee sur des donnees physiologiques et clinques recentes. Perspectives d'avenir, Contracept, Fertil., Sex., 21(Suppl No. 4):2-7 (1993).

Baird, DT, Gonadotrophins: past, present and future, Chp. 37:459-465 (1993).

Hull, M. L., The effect of recombinant follicle stimulating hormone (Gonal-F) on endogenous luteinizing hormone secretion in women, Human Reproduction, 13(5):1139-1143 (1998).

* cited by examiner

GONADOTROPHINS IN THE TREATMENT ANOVULATORY WOMEN

REFERENCE TO RELATED APPLICATIONS

The present application is the national stage under 35 U.S.C. 371 of international application PCT/GB00/01745, filed May 5, 2000 which designated the United States, and which international application was published under PCT Article 21(2) in the English language.

The present invention relates to the use of gonadotrophins in the treatment of anovulatory women. In particular, it relates to the use of luteinising hormone (LH) for promoting follicular development, and especially paucifollicular and monofollicular development, when inducing ovulation in anovulatory women.

Gonadotrophins are widely used in clinical practice to treat women with WHO group II and WHO group I anovulation (World Health Organisation Technical Report 514, (1973)). Conventionally, folliculogenesis is induced by administering hMG (human menopausal gonadotrophin) or u-hFSH (urinary human follicle stimulating hormone) at a dose of 75-150 IU/day. This dose is increased after a few days (usually five) by steps of 75 IU. It is rare to exceed 450 IU/day. When there is at least one follicle having a mean diameter of at least 18 mm and no more than two follicles having a mean diameter of at least 16 mm, a high dose (of 5000 IU for example) of hCG (human chorionic gonadotrophin) is administered to induce ovulation. This "conventional protocol" has been used successfully for more than 20 years. It carries some risks however, mainly in patients with polycystic ovarian disease (PCOD). These risks include the occurrence of ovarian hyperstimulation syndrome (OHSS), and a relatively high incidence of multiple pregnancies (Schenker et al, *Fertil. Steril.* 35:105-123 (1981)). Although the majority of multiple pregnancies are twins, induction of ovulation contributes to one third of the high rank multiple births in the UK (Levene et al, *Br. J. Obstet. Gynacol.* 99:607-613 (1992)).

Careful monitoring during treatment by ultrasound (US) and assessment of serum oestradiol ($E_2$) have reduced these risks but have not been able to prevent them in all patients. These problems are directly related to the difficulty of obtaining the growth of a single dominant follicle leading to non-physiological multifollicular development.

During the last 10 years, a new protocol has been designed (the "chronic low dose protocol") and tested in order to reduce further the incidence of the complications of gonadotrophin therapy (Seibel et al, *Int. J. Fertil.*, 29:338-339 (1984); Buvat et al, *Fertil. Steril.*, 52:553-559 (1989); Hamilton-Fairley et al, *Human Reprod* 6:1095-1099 (1991); Sagle et al, *Fertil Steril.*, 55:56-60 (1991); Shoham et al, *Fertil. Steril.*, 55:1051-1056 (1991); Meldrum, *Fertil Steril.*, 55:1039-1040 (1991)). This protocol starts with a low dose of FSH or hMG (75 IU/day) and no dose adjustment before seven or preferably 14 days of treatment. If a dose adjustment is required, this is made by incremental steps of only 37.5 IU. In addition, each subsequent increase may only be effected after seven days of treatment at a given dose. The concept of this chronic low dose protocol is to find the threshold amount of FSH necessary to promote unifolliculogenesis. Encouraging results have been published so far, showing that this approach reduces the mean number of preovulatory follicles, the average preovulatory $E_2$ level and the size of the ovary at mid-luteal phase.

However, despite the use of the chronic low dose protocol, some treatment cycles still have to be cancelled due to an over-response (e.g. where there are more than 3 follicles with a mean diameter of 16 mm or more). In addition, the multiple pregnancy rate, although clearly improved when compared to the conventional protocol, is still higher than in spontaneous conception cycles i.e. 5-10% in induced ovulation as opposed to 1.5% in spontaneous cycles. This is due to the fact that development of a single pre-ovulatory follicle is obtained in only about two thirds to three quarters of the induced cycles and follicles having a mean diameter of 15 mm or less are usually not considered when assessing the number of pre-ovulatory follicles on the day of hCG administration (Buvat et al, *Fertil. Steril.*, 52:553-559 (1989); Hamilton-Fairley et al, Human Reprod. 6:1095-1099 (1991)). It is however not clear whether follicles with a mean diameter of 14 to 15 mm, or even less, on the day of hCG administration, will ovulate and lead to the release of a healthy fertilisable oocyte. Thus, it would be desirable to have improvements in FSH-induced follicular development treatment in which the rates of multiple pregnancy and cycle cancellation are reduced.

Antral follicle growth is induced by FSH. Continuously throughout life and up to the menopause, some follicles enter a growth phase which is interrupted by regression and atresia before reaching the full maturity stage of preovulatory status (Hillier, *Hum. Reprod.*, 9:181-191 (1994)). During the growth phase, any follicle could be rescued from atresia, provided that it is exposed to a sufficient concentration of FSH. The level of FSH required to prevent atresia and promote further growth of a follicle is called the "FSH threshold" level (Brown, *Aus. NZ J. Obstet. Gynecol.*, 18: 47-55 (1987). The FSH threshold level varies with time and, at a given time-point, the follicles which are currently in a growth phase have different FSH threshold levels, This is the rationale on which the "chronic low dose" protocol is based. A progressive and cautious increase in the dose of FSH is used for finding the threshold level of a minimal number of follicles, and hopefully achieving mono-ovulation.

It is known that luteinising hormone (LH) also contributes to the phenomenon of follicle dominance and mono-ovulation. Indeed, although some LH is essential for oestrogen synthesis during folliculogenesis, there is evidence that excessive exposure to LH will trigger follicular atresia and suppress granulosa proliferation. Developing follicles appear thus to have finite requirements for stimulation by LH, beyond which normal follicular development ceases. This is the "LH ceiling" concept (Hillier, *Hum. Reprod*, 9:181-191 (1994)). It is believed that, at a given time-point, the follicles which are currently in a growth phase have different LH ceiling levels. It is suggested that the more mature follicles are more resistant to the atretic action of LH than less mature follicles.

Two cases of WHO group I anovulation treated by either FSH alone or hMG using a step-up protocol have been reported (Glasier et al, *Journal of Endocrinology*, 119 A-159 (1988)). The "FSH alone" cycle had a much larger number of mature follicles than the hMG cycle, possibly supporting a role of LH in the atresia of secondary follicles. Afterwards two comparative studies were published. In a first cross-over study in 10 hypogonadotrophic hypogonadal women, a striking difference was recorded in terms of preovulatory $E_2$ levels, but follicular count was not reported (Couzinet et al, *J. Clin. Endocrinol. Metab.* 66:552-556 (1988)). A second cross-over study in 9 hypogonadotrophic hypogonadal women reported a mean number of follicles having a mean diameter of more than 16 mm on the day of hCG administration of 2.0 (0.7 in hMG-treated cycles and of 1.2 in FSH-treated cycles (Shoham et al, *Fertil. Steril.*, 55:1051-1056 (1991)). No information is available on the number of smaller follicles.

More recently, the results of administering 150 IU hFSH (human FSH) and 75 IU r-hLH (recombinant human LH) to a single patient with unmeasurably low serum FSH, LH and oestradiol concentrations have been published (Hall et al, *The Lancet*, 344(8918):334-335 (1994)). Administration of r-hLH and hFSH caused $E_2$ levels to be raised, and the total number of follicles of 10 mm or more in diameter to be reduced, as compared to administration of hFSH alone. However, the number of large follicles remained sufficiently high to suggest an unacceptably high multiple pregnancy rate.

A further study compared the effect of administering r-hLH (at a dose of either 300 IU/day or 750 IU/day) and r-hFSH to normal ovulatory women after treatment with FSH for stimulating multiple follicular development prior to intrauterine implantation (Sullivan et al, *Journal of Clinical Endocrinology and Metabolism*, 84, 228-232, 1999)). The results indicate that serum $E_2$ levels were raised in those women who received LH, although no measurements of the number and size of follicles were made and a multiple pregnancy occurred in the group receiving 750 IU/day of LH.

According to a first aspect of the present invention, there is provided the use of LH and/or a biologically-active analogue thereof in the production of a medicament for inducing folliculogenesis in anovulatory women at a daily dose in the range of from 100 to 1500 IU.

As used herein, an "IU ratio" is the ratio of the number of IU of one component to the number of IU of another component. It is noteworthy that gonadotrophins may now be expressed in (mass/μg) instead of biological IU. In this case, a conversion factor has to be used to translate the new value into IU. For convenience, references hereinafter to LH, FSH and hCG are intended to include biologically-active analogues thereof.

The inventors have found that the administration of LH at a dose of 100 to 1500 IU/day can promote paucifollicular development, that is to say, it can reduce the number of preovulatory follicles per treatment cycle in patients undergoing follicular induction, as compared to cycles where LH is not administered at a dose of 100 to 1500 IU/day. LH administered in accordance with the invention can induce unifolliculogenesis, i.e. the development of a single preovulatory follicle. Doses in the range of from 200 to 800 IU/day, and more preferably 225 to 450 IU/day, have been found to be particularly effective. The reduction in multifollicular development can reduce the number of cycles cancelled owing to excessive follicle development, i.e. it can rescue those cycles when there are an excessive number of follicles, making the process of ovulation induction more efficient. In addition, the incidence of multiple pregnancy and of OHSS can be reduced.

Figure 1:
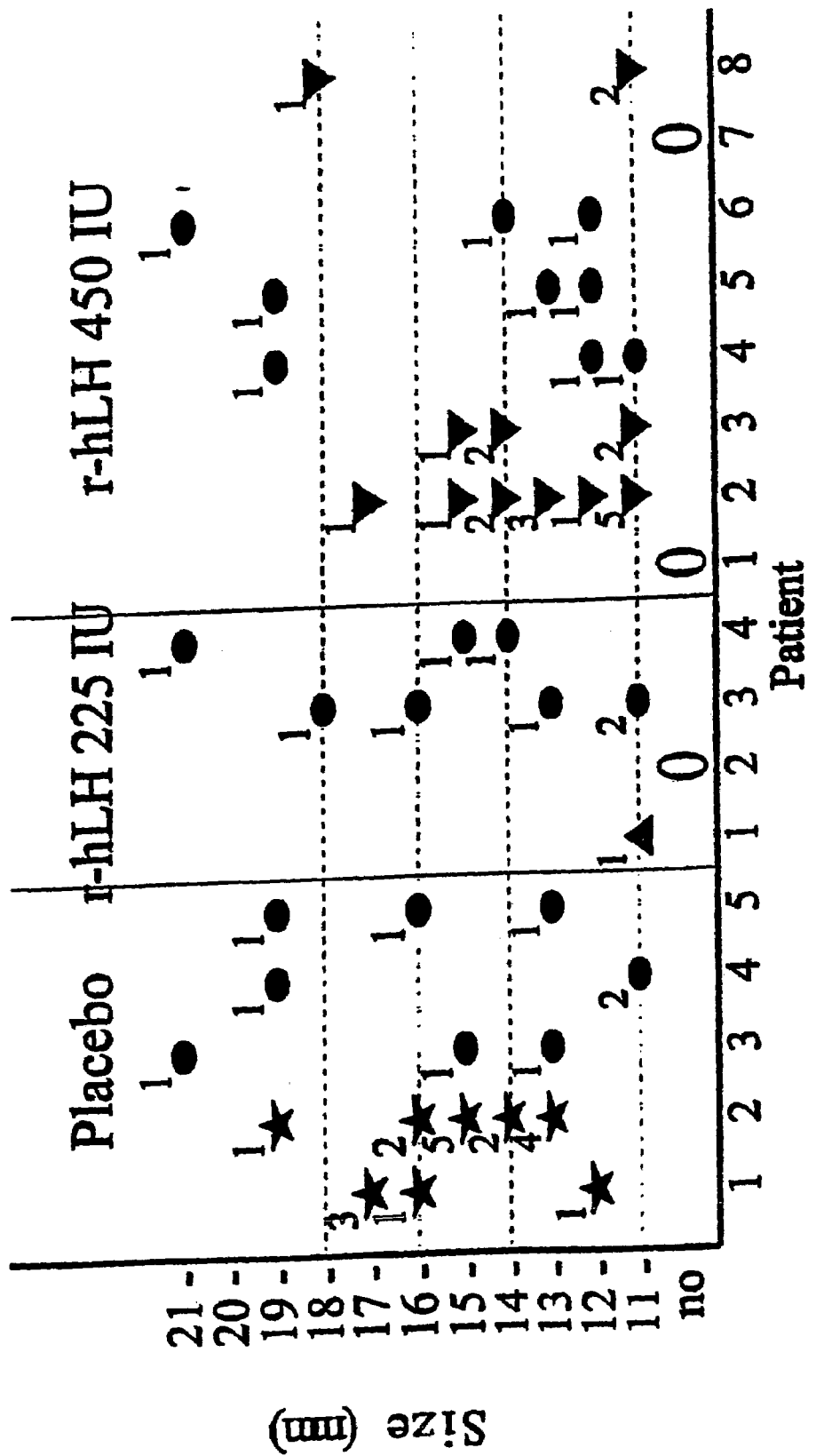
FIG. 1 shows the size and number of follicles on the day of hCG administration (or the last day of treatment if no hCG was administered) for each of the patients.

The required daily dose may be administered as a single dose each day. Thus, the medicament may be packaged so as to provide only the daily dose of LH, e.g. in a unit-dose container such as a vial. However, it is possible that LH may be administered on two or more occasions during the day—provided of course that total LH administered during the day equals the daily dose—and the medicament packaged accordingly, i.e. in a multi-dose container. It is also possible that LH could be administered on alternate days or at even longer intervals. Such decisions will be taken by the physician administering the medicament and will depend on parameters such as the patient's body mass index (BMI), medical history, stage of follicular development when receiving LH, metabolism, response to the treatment, the half-life of the medicament and so on.

Folliculogenesis will generally be induced in anovulatory women by the administration of FSH using the conventional protocol or the chronic low dose protocol described above or an alternative protocol. LH should be administered at an appropriate stage of follicular development, e.g. the mid- to late-follicular phase. This stage may be decided by the physician administering the medicament and may depend on the regime by which ovulation is induced. By way of example, the appropriate stage of follicular development may be judged to have been reached when at least a single follicle reaches a mean diameter of 8 mm, or when at least one follicle has a mean diameter in the range 10-15 mm (preferably 1-14 mm), or when there are more than 3 follicles with a mean diameter in the range of from 8 to 13 mm and no larger follicles.

The administration of LH will generally cease when ovulation is induced by the administration of the high dose of hCG. Again, the timing of hCG administration to induce ovulation may be decided by the physician. For example, it may be when there is at least one follicle having a diameter of 18 mm or more and no more than 3, preferably 2, follicles having a diameter of 11 mm or more.

LH can be administered only when the required stage of follicular development has been reached. In this case, the administration of FSH can be discontinued altogether or can be continued at the same dose as before, or at a lower or higher dose. It is preferred if the administration of FSH is continued but at a lower dose than previously, the dose being lower than that of LH.

Alternatively, LH can be administered concomitantly with the conventional or chronic low dose protocols, i.e. prior to follicular development reaching an appropriate stage. When the required stage of follicular development has been reached, the administration of FSH can be discontinued or continued as before, or at a lower or higher dose, provided that LH is administered at the appropriate dose. In a further alternative, the medicament may formulated such that it can be used in a procedure which replaces the conventional or chronic low dose protocols.

Thus, FSH and/or a biologically-active analogue thereof may be used in the production of the medicament. In this embodiment, the IU ratio of LH to FSH is preferably in the range of from 1.5:1 to 20:1. More preferably, the ratio is in the range of from 1.5:1 to 10:1.

When the medicament is for administration after the appropriate stage of follicular development has been reached, the IU ratio of LH:FSH may be about 10:1. A particularly preferred daily dose for such a medicament is 375 IU of r-hLH and 37.5 IU of r-hFSH.

According to a second aspect of the invention, there is provided the use of LH and FSH and/or biologically-active analogues thereof in the production of a medicament for inducing folliculogenesis in women at an IU ratio of LH to FSH in the range of from 1.5:1 to 20:1.

The uses of the first and second aspects of the invention may be modified in that LH is replaced by an equivalent dose of hCG and/or a biologically-active analogue thereof.

As used herein, an "equivalent dose" of human chorionic gonadotrophin (hCG) is calculated on the basis that 1 IU of hCG is equivalent to 5-7 IU of LH in the pharmacopaeia Van Hell bioassay (Van Hell, H, et al, Effects of human menopausal gonadotrophin preparations in different bioassay methods, *Acta Endocrin.*, 47: 409-418, 1964). For convenience, references herein to luteinising hormone (LH) are intended to include hCG, with doses of LH being intended to include the equivalent dose of hCG.

According to a third aspect of the invention, there is provided a product containing LH (or an equivalent dose of hCG) and FSH and/or biologically-active analogues thereof as a combined preparation for simultaneous, sequential or separate use in inducing folliculogenesis in women, the preparation comprising LH (or an equivalent dose of hCG) and FSH and/or biologically-active analogues thereof at an IU ratio of LH (hCG) to FSH in the range of from 1.5:1 to 20:1.

In accordance with the second and third aspects of the invention, LH or hCG and FSH may be administered to anovulatory women, preferably throughout the cycle up until the induction of ovulation by the administration of the high dose of hCG. Alternatively, they may be administered after follicular development has reached an appropriate stage.

The invention also provides a method for the induction of folliculogenesis in anovulatory women, including the administration of luteinising hormone and/or a biologically-active analogue thereof at a dose in the range of from 100 to 1500 IU/day or an equivalent dose of human chorionic gonadotrophin and/or a biologically-active analogue thereof.

LH, FSH and hCG may be obtained from natural sources, e.g. isolated from urine, pituitary or placenta, or may be obtained using recombinant DNA technology (see WO85/01959 and Loumaye et al, *Human Reprod*, 11: 95-107, 1996). Biologically-active analogues thereof include peptidic analogues, non-peptidic analogues and chimeras. It is preferred if human LH and FSH are used in the present invention.

Compounds useful in the invention may be formulated for administration by any convenient route, often in association with a pharmaceutically and/or veterinarily acceptable carrier. It is preferred that the compounds are formulated for parenteral administration.

It is preferred that the LH and FSH (when present) be administered subcutaneously, preferably into the anterior abdominal wall.

Formulations for parenteral administration will usually be sterile. Pharmaceutical formulations adapted for parenteral administration include aqueous and non-aqueous sterile injection solutions which may contain anti-oxidants, buffers, bacteriostats and solutes which render the formulation isotonic with the blood of the intended recipient; aqueous and non-aqueous sterile suspensions which may include suspending agents and thickening agents are also within the scope of the invention. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets. The formulations can be administered through a prefilled syringe, an auto-injector or a multidose auto-injector.

Oral and other enteral formulations need not be sterile and may be presented in unit- or multi-dose form. Oral formulations may be in the form of solids, such as powders, granules, tablets, capsules (for example hard or soft gelatin capsules) or lozenges, or liquids, such as syrups or elixirs. Fillers and/or carriers may be present as appropriate, and those skilled in the art of pharmaceutical formulation will be able to provide such additional or alternative excipients as may be necessary or desirable; flavouring agents are one example. Any formulation intended for oral administration may be formulated for enteric resistance, so as to assist delivery to the small intestine by avoiding or mitigating any digestion of the compound(s) as may occur in the stomach or the proximal part of the small intestine. Tablets or capsules may be enteric coated, for example by conventional procedures. Liquid formulations may be effectively rendered enteric resistant by including or being co-administered with a suitable agent such as medium-chain triglycerides.

Enteral compositions other than oral compositions include rectal compositions, which may be in the form of a suppository. Suppositories will generally include a suppository base, such as cocoa butter. Again, particular formulations containing the active ingredient(s) may routinely be prepared by those skilled in the art of pharmaceutical formulation.

Preferred features of each aspect of the invention are as for each other aspect, mutatis mutandis.

All patent and literature documents referenced throughout this specification are hereby incorporated by reference to the fullest extent allowed by law.

The invention will now be described further in the following non-limiting examples.

EXAMPLE 1

The effect of LH when administered after FSH stimulation was examined on WHO Group II anovulatory women during a clinical study conducted according to ICH GCP (International Conference on Harmonisation—Good Clinical Practice) guidelines. The patients had the following characteristics:

Premenopausal; aged between 18 and 39; infertile due to ovulatory dysfunction; have had spontaneous menses, menses induced by clomiphene citrate therapy or a positive progestin-induced withdrawal bleed within the previous year; a body mass index of 35 or less (calculated as body weight in kg divided by (height×weight) in $m^2$); euthyroid; no medical condition which may interfere with the absorption, distribution, metabolism or excretion of LH; no clinically systemic disease; no known allergy to gonadotrophin preparations; no persistent ovarian cyst of 11 mm or greater or ovarian endometrioma (as determined by ultrasound); no previous or current hormone dependent tumour; no clinically relevant reproductive tract disease; and no active substance abuse.

The patients underwent routine ovulation induction with FSH until there were 4 or more follicles in the range of from 8-13 mm in diameter, no larger follicles and an endometrium of 8 mm or more thickness. They were then randomised into 3 blinded groups, one to receive a placebo, one to receive 225 IU/day of r-hLH and one to receive 450 IU/day of r-hLH.

Table 1 below summarises the respective groups of patients:

TABLE 1

| Mean ± SD | Placebo | r-hLH 225 IU/day | r-hLH 450 IU/day |
|---|---|---|---|
| No of patients | 5 | 4 | 8 |
| Age (yrs) | 29.2 ± 5.7 | 26.8 ± 6.2 | 30.9 ± 3.9 |
| (min-max) | (23-35) | (20.35) | (25-38) |
| Weight (kg) | 62.8 ± 15.9 | 60.0 ± 1.6 | 66.8 ± 15.4 |
| (min-max) | (47-86) | (58-62) | (48-97) |
| BMI | 24.6 ± 4.7 | 22.8 ± 1.9 | 24.7 ± 4.9 |
| (min-max) | (20-31) | (21-25) | (18-34) | r-hLH (LHadi®, Serono) was used in vials containing 75 IU r-hLH and 47.75 mg of sucrose, phosphate buffer and Tween 20 in a lyophilised form. LHadi is produced in genetically engineered Chinese hamster Ovary (CHO) cells in which the genes encoding the alpha and beta chains of human LH have been introduced through recombinant technology. The specific activity of LHadi is approximately 15000 IU LH/mg.

For a dose of 225 IU, 3 vials were used. One vial was reconstituted in 1 ml of water and gently agitated, taking care to avoid contact with the rubber stopper. The totality of the resulting solution was aspirated and used for reconstitution of the second vial. After gentle agitation, the totality of the resulting solution was aspirated and used for reconstitution of the third vial. After further gentle agitation, the totality of the resulting solution was aspirated and immediately injected subcutaneously in the anterior abdominal wall using a new needle. For a dose of 450 IU, two injections of 225 IU were made.

The placebo was in vials matching the r-hLH vials but containing only sucrose, phosphate buffer and Tween 20.

The r-hLH/placebo treatment was continued for 7 days unless at least one follicle reached a mean diameter of at least 18 mm and there were 3 or fewer follicles having a mean diameter of 11 mm or greater. In this case, a single dose of 5000 IU of u-hCG (PROFASI, Serono) was given subcutaneously.

Prior to and during the r-hLH/placebo treatment, ultrasound (US) was used at intervals of 1-2 days to measure the mean diameter of the follicles (determined as the mean of the two longest perpendicular diameters) and the endometrial thickness (assessed as the distance from the hyperechogenic interface of the endometrium and the myometrium to the opposite interface including the stronger midline echo (endometrial interface)). All follicles with a mean diameter of 11 mm or greater were recorded.

Prior to and each time an ultrasound scan was carried out during the r-hLH/placebo treatment, a blood sample was taken and the resulting serum was analysed for $E_2$ (oestradiol), $P_4$ (progesterone), LH, FSH and androstenedione.

$E_2$ and $P_4$ were analysed using DPC Coat-a-count, RIA solid phase coated tube separation, LH (serum and urinary) and FSH were analysed using MAIACLONE IRMA, and androstenedione was analysed using Diagnostic System Laboratories method, RIA.

The results are summarised in Tables 2-4 and in FIG. 1 of the accompanying drawings which is a graph showing the size and number of follicles on the day of hCG administration (or the last day of treatment of no hCG was administered) for each of the patients.

It can be seen that the administration of LH at 225 or 450 IU/day subsequent to FSH treatment resulted in a more marked follicular regression than in the administration of placebo, as suggested by patients with complete follicular regression, a smaller number of follicles on the day of hCG administration and a reduction in follicle median size from 15 mm in the placebo group to 14 nm in the 225 IU r-hLH group and 13 mm in the 450 IU r-hLH group.

The efficacy of r-hLH in promoting mono-ovulation is illustrated by the emergence of a dominant follicle (as evidenced by the median size), the absence of follicular phase luteinisation and a comparatively lower $P_4$ level at the mid-luteal phase.

EXAMPLE 2

The effect of LH and FSH administered during the late follicular phase was examined on WHO Group I anovulatory women during a clinical trial conducted according to ICH GCP guidelines. The patients had the following characteristics:

premenopausal; aged between 18 and 39; a clinical history of hypogonadotrophic hypogonadism; have stopped treatment (if any) with pulsatile GnRH, gonadotrophins or oestrogen progesterone treatment therapy at least one month before the screening procedure; have had a negative progesterone challenge test performed curing the screening period, had the following hormonal values in a fasting blood sample (between 7 and 9.30 AM) drawn within 6 months before the treatment period:

| | |
|---|---|
| FSH: | <5 mIU/ml |
| LH: | <1.2 mIU/ml |
| Thyroid stimulating hormone (TSH): | <6.5 μIU/ml |
| Free $T_4$: | >11 and <24 pmol/l |
| Testosterone: | <3-5 nmol/l |
| Prolactin (PRL): | <520 mIU/l; | no clinically significant abnormal finding, within 6 months prior to study start, in pre-treatment haematology, in clinical chemistry and urinalysis parameters or results of no pathological significance of outside normal limits; have, on file, if clinically indicated, a CT scan or MRI of the hypothalamic pituitary region to document current putative tumoral status of the region; a body mass index of between 18.4 (percentile 10 for 18 years) and 31.4 (percentile 90 for 38 years); no medical condition which may interfere with the absorption, distribution, metabolism or excretion of LH or FSH; no clinically systemic disease; no known allergy to gonadotrophin preparations; no persistent ovarian cyst of 11 mm or greater or ovarian endometrioma (as determined by ultrasound); no previous or current hormone dependent tumour; no clinically relevant reproductive tract disease; and no active substance abuse.

The study was divided into an open phase of a maximum of 28 days and a blinded phase of a maximum of 7 days.

In the open phase, all patients received 225 IU/day of r-hLH and 112.5 IU/day of r-hFSH. If there was no rise in $E_2$ levels or sign of follicular growth after 7 days, the dose of r-hFSH was raised to 150 IU/day. After a further 7 days, the dose of r-hFSH was raised to 187.5 IU/day if there was no rise in $E_2$ levels or sign of follicular growth and after a further 7 days, the dose of r-hFSH was raised to 262.5 IU/day if there was no rise in $E_2$ levels or sign of follicular growth. The dose of r-hLH remained constant throughout the open phase.

When a patient had at least one follicle with a mean diameter in the range of from 10-13 mm, she entered the blinded phase. In this phase, the patients were randomised into 3 blinded groups, one to receive a LH placebo and continue the dose of r-hFSH received on the last day of the open phase, one to receive 225 IU/day of r-hLH and continue the dose of r-hFSH received on the last day of the open phase, and one to receive 225 IU/day of r-hLH and a FSH placebo.

Table 5 below summarises the respective groups of patients.

TABLE 5

| Mean ± SD | FSH/Placebo | r-hLU/placebo | FSH/r-hLH |
|---|---|---|---|
| No of patients | 6 | 6 | 8 |
| Age (yrs) | 31.9 ± 6.2 | 31.0 ± 3.0 | 30.8 ± 4.6 |
| (min-max) | (21-39) | (27-34) | (25-37) |
| Weight (kg) | 70.3 ± 10.0 | 51.7 ± 4.4 | 66.9 ± 15.9 |
| (min-max) | (60-88) | (46-59) | (50-89) |
| BMI | 25.2 ± 2.3 | 19.8 ± 1.1 | 24.6 ± 4.3 |
| (min-max) | (21-28) | (19-21) | (20-30) | r-hFSH (GONAL-F, Serono) was used in ampoules containing 75 IU r-hFSH and 30 mg sucrose and phosphate buffer in a lyophilised form, up to 3 of which were dissolved in 1 ml of water for injection. Matching ampoules containing only sucrose and phosphate buffer were provided for the FSH placebo.

r-hLH (LHADI, Serono) was provided and administered as in Example 1. The LH placebo was in vials matching the r-hLH vials but containing only sucrose, phosphate buffer and TWEEN 20.

All injections were made subcutaneously into the anterior abdominal wall.

The blinded phase was continued for 7 days unless at least one follicle reached a mean diameter of at least 18 mm and there were 2 or fewer follicles having a mean diameter of 11 mm or greater. In this case, a single dose of 10000 IU of u-hCG (PROFASI, Serono) was given subcutaneously.

On the first, fifth and eight days of the open phase, and at regular intervals (i.e. 1 to 2 days) during the blinded phase, ultrasound was used to measure the mean diameter of the follicles and the endometrial thickness. All follicles with a mean diameter of 11 mm or greater were recorded.

On the first day of the open phase, and at regular intervals (i.e. 1 to 2 days) during the blinded phase, a blood sample was taken and the resulting serum was analysed for $E_2$, $P_4$, LH, FSH and androstenedione as in Example 1.

Figure 2:
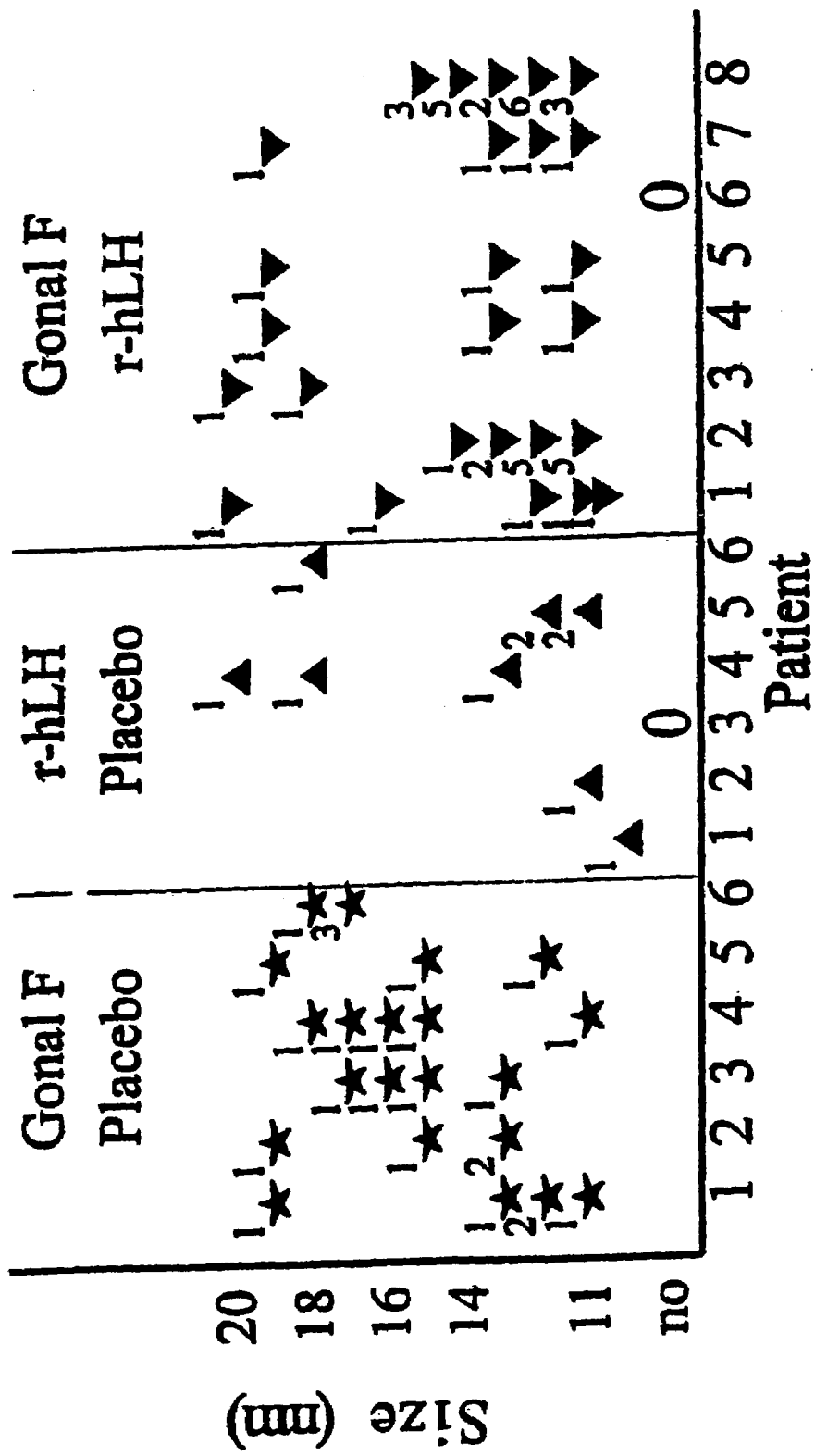
FIG. 2 shows the size and number of follicles on the day of hCG administration (or the last day of treatment if no hCG was administered) for each of the patients.

The results are summarised in Tables 6-9 and in FIG. 2 of the accompanying drawings which is a graph showing the size and number of follicles on the day of hCG administration (or the last day of treatment of no hCG was administered) for each of the patients.

It can be seen that stopping FSH and administering r-hLH at 225 IU/day resulted in a marked and excessive follicular regression.

The efficacy of r-hLH in promoting mono-ovulation in the presence of FSH is illustrated by a reduction in the mean number of follicles having a diameter of 14 mm or greater, an increase in the proportion of patients with only 1 or 2 follicles having a diameter of 14 mm or greater, the emergence of a dominant follicle (as evidenced by a median follicle size of 12 mm as compared to 15 mm for the FSH/placebo group), and the absence of follicular phase luteinisation.

TABLE 2

Summary Data on Number and Size of Follicles and hCG Cancellation

| Treatment Group | Patient Id | Number of Follicles >= 8 mm at Baseline | Number of Follicles >= 11 mm Last US | Number of Follicles >= 14 mm Last US | hCG Received | Reason/Comment |
|---|---|---|---|---|---|---|
| Placebo | 20002 | 8 | 5 | 4 | No | Risk of OHSS |
| | 30003 | 22 | 14 | 10 | Yes | |
| | 40001 | 20 | 3 | 2 | Yes | |
| | P40005 | 12 | 3 | 1 | Yes | |
| | P40008 | 8 | 3 | 2 | Yes | |
| | N = 5 | 14.00 ± 6.63 | 5.60 ± 4.77 | 3.80 ± 3.63 | 4 Yes/1 No | |
| r-hLH 225 IU/day | 20001 | 5 | 1 | 0 | No | Follicles regressed |
| | 30001 | 12 | 0 | 0 | No | Failure of treatment |
| | 40003 | 18 | 5 | 2 | Yes | |
| | 40007 | 4 | 3 | 3 | Yes | |
| | N = 4 | 9.75 ± 6.55 | 2.25 ± 2.22 p = 0.4391 | 1.25 ± 1.50 p = 0.2342 | 2 Yes/2 No | |
| r-hLH 450 IU/day | 10001 | 6 | 0 | 0 | No | all follicles became atretic |
| | 20003 | 10 | 13 | 4 | No | Risk of OHSS |
| | 30002 | 9 | 5 | 3 | No | Failure of treatment |
| | 40002 | 17 | 3 | 1 | Yes | |
| | 40004 | 7 | 3 | 1 | Yes | |
| | 40009 | 4 | 3 | 2 | Yes | |
| | 50001 | 9 | 0 | 0 | No | Failure of treatment |
| | 70001 | 9 | 3 | 1 | Yes | |
| | N = 8 | 8.88 ± 3.83 | 3.75 ± 4.10 p = 0.8684 | 1.50 ± 1.41 p = 0.2731 | 4 Yes/4 No | | p-values from comparison with placebo group (ANCOVA adjusted for number of follicles at baseline)
P pregnant patient

TABLE 3

Number of Patients with 0, 1, 2, 3, or >3 Follicles on the Day of hCG or on the Last Day of Treatment if No hCG was Administered

| | | Treatment Randomised | | | | | | | p-values | | | |
| | | Placebo | | r-hLH 225 IU/day | | r-hLH 450 IU/day | | | One-sided | | Two-sided | |
| Variable | Number of Follicles | N | % | N | % | N | % | Contrast** | Asymptotic | Exact | Asymptotic | Exact |
|---|---|---|---|---|---|---|---|---|---|---|---|---|
| Follicles >= 11 mm | 0 foll. >= 11 mm | 0 | 0.0% | 1 | 25.0% | 2 | 25.0% | Placebo vs. r-hLH 225 IU | 0.0562 | 0.1429 | 0.1124 | 0.1746 |
| | 1 foll. >= 11 mm | 0 | 0.0% | 1 | 25.0% | 0 | 0.0% | Placebo vs. r-hLH 450 IU | 0.1108 | 0.2339 | 0.2217 | 0.3590 |
| | 2 foll. >= 11 mm | 0 | 0.0% | 0 | 0.0% | 0 | 0.0% | r-hLH 225 IU vs. r-hLH 450 IU | 0.2987 | 0.3879 | 0.5973 | 0.7192 |
| | 3 foll. >= 11 mm | 3 | 60.0% | 1 | 25.0% | 4 | 50.0% | Overall comparison | 0.2064 | 0.2222 | 0.4128 | 0.4378 |
| | >3 foll. >= 11 mm | 2 | 40.0% | 1 | 25.0% | 2 | 25.0% | | | | | |
| | All | 5 | 100.0% | 4 | 100.0% | 8 | 100.0% | | | | | |
| Follicles >= 14 mm | 0 foll. >= 14 mm | 0 | 0.0% | 2 | 50.0% | 2 | 25.0% | Placebo vs. r-hLH 225 IU | 0.0774 | 0.1429 | 0.1547 | 0.2857 |
| | 1 foll. >= 14 mm | 1 | 20.0% | 0 | 0.0% | 3 | 37.5% | Placebo vs. r-hLH 450 IU | 0.0817 | 0.1298 | 0.1635 | 0.2416 |
| | 2 foll. >= 14 mm | 2 | 40.0% | 1 | 25.0% | 1 | 12.5% | r-hLH 225 IU vs. r-hLH 450 IU | 0.3786 | 0.4788 | 0.7572 | 0.8323 |
| | 3 foll. >= 14 mm | 0 | 0.0% | 1 | 25.0% | 1 | 12.5% | Overall comparison | 0.1259 | 0.1354 | 0.2519 | 0.2675 |
| | >3 foll. >= 14 mm | 2 | 40.0% | 0 | 0.0% | 1 | 12.5% | | | | | |
| | All | 5 | 100.0% | 4 | 100.0% | 8 | 100.0% | | | | | |

Contrast**
Overall Comparison: Jockheere-Terpstra test
Pairwise Comparison: Cochran-Armitage test for trend.

TABLE 4

Descriptive Statistics of Hormone Levels Measured at T1 and on the Day of hCG or on the Last Day of Treatment if No hCG was Administered

| | | T1 (first day of stimulation) | | | | | | Day of hCG or last day of treatment if no hCG was administered | | | | | |
| Variable | Treatment | n | Mean | SD | SEM | Median | Range | n | Mean | SD | SEM | Median | Range |
|---|---|---|---|---|---|---|---|---|---|---|---|---|---|
| FSH (IU/L) | Placebo | 5 | 12.20 | 5.60 | 2.50 | 9.50 | (8-21) | 5 | 6.54 | 3.84 | 1.72 | 7.90 | (2-11) |
| | r-hLH 225 IU/day | 4 | 12.53 | 6.75 | 3.37 | 11.45 | (6-21) | 4 | 7.35 | 2.98 | 1.49 | 6.05 | (6-12) |
| | r-hLH 450 IU/day | 7 | 11.10 | 3.71 | 1.40 | 9.80 | (8-19) | 8 | 6.94 | 2.05 | 0.73 | 6.25 | (5-10) |
| | All | 16 | 11.80 | 4.84 | 1.21 | 9.65 | (6-21) | 17 | 6.92 | 2.70 | 0.66 | 6.20 | (2-12) |
| LH (IU/L) | Placebo | 5 | 7.84 | 6.30 | 2.82 | 4.80 | (3-18) | 5 | 6.12 | 2.74 | 1.23 | 6.90 | (2-9) |
| | r-hLH 225 IU/day | 4 | 5.25 | 2.69 | 1.34 | 6.20 | (1-7) | 4 | 6.80 | 4.48 | 2.24 | 6.40 | (2-12) |
| | r-hLH 450 IU/day | 7 | 4.60 | 4.14 | 1.57 | 3.40 | (1-13) | 7 | 6.67 | 4.14 | 1.56 | 4.80 | (3-15) |
| | All | 16 | 5.78 | 4.58 | 1.15 | 4.55 | (1-18) | 16 | 6.53 | 3.60 | 0.90 | 6.00 | (2-15) |
| E2 (pmol/L) | Placebo | 5 | 4031.6 | 3759.9 | 1681.5 | 3612.0 | (598-10017) | 5 | 4780.6 | 4612.7 | 2062.9 | 3540.0 | (313-11040) |
| | r-hLH 225 IU/day | 4 | 1491.8 | 1633.5 | 816.0 | 851.5 | (384-3880) | 4 | 2560.0 | 4715.7 | 2357.8 | 227.0 | (153-9633) |
| | r-hLH 450 IU/day | 7 | 1376.7 | 885.8 | 334.8 | 1315.0 | (123-2809) | 8 | 1966.9 | 2665.1 | 942.3 | 297.0 | (133-7269) |
| | All | 16 | 2235.1 | 2486.8 | 621.7 | 1304.5 | (123-10017) | 17 | 2934.0 | 3763.6 | 912.8 | 378.0 | (133-11040) |
| P4 (nmol/L) | Placebo | 5 | 4.56 | 1.80 | 0.80 | 4.30 | (3-7) | 5 | 8.86 | 10.83 | 4.84 | 4.50 | (2-28) |
| | r-hLH 225 IU/day | 4 | 3.08 | 1.02 | 0.51 | 3.05 | (2-4) | 4 | 2.68 | 1.15 | 0.57 | 2.50 | (2-4) |
| | r-hLH 450 IU/day | 7 | 2.47 | 1.03 | 0.39 | 2.30 | (1-4) | 8 | 2.89 | 1.73 | 0.61 | 2.25 | (1-6) |
| | All | 16 | 3.28 | 1.53 | 0.38 | 2.85 | (1-7) | 17 | 4.59 | 6.24 | 1.51 | 2.80 | (1-28) |
| Androstenedione (nmol/L) | Placebo | 5 | 17.42 | 11.62 | 5.20 | 16.50 | (5-35) | 5 | 15.74 | 7.03 | 3.14 | 14.40 | (8-27) |
| | r-hLH 225 IU/day | 4 | 8.63 | 0.88 | 0.44 | 8.30 | (8-10) | 4 | 11.75 | 1.92 | 0.96 | 12.00 | (9-14) |
| | r-hLH 450 IU/day | 7 | 10.53 | 7.11 | 2.69 | 8.00 | (5-26) | 8 | 12.18 | 9.56 | 3.38 | 8.95 | (6-35) |
| | All | 16 | 12.21 | 8.38 | 2.09 | 9.10 | (5-35) | 17 | 13.12 | 7.49 | 1.82 | 11.40 | (6-35) |

TABLE 6

Summary Data on Stimulation Open and Blinded Phases and hCG Cancellation

| | | Open Phase | | | | |
| Treatment Group | Patient Id | First Dose of FSU (IU) | Last Dose of FSH (IU) | Number of Days | Cumulative FSH Dose | Cumulative LH Dose |
|---|---|---|---|---|---|---|
| Gonal-F/Placebo | 10002 | 112.5 | 112.5 | 8 | 900 | 1800 |
| | 10004 | 112.5 | 150.0 | 13 | 1688 | 2925 |

TABLE 6-continued

Summary Data on Stimulation Open and Blinded Phases and hCG Cancellation

|  | 20001 | 112.5 | 112.5 | 7 | 788 | 1575 |
|---|---|---|---|---|---|---|
|  | 30002 | 112.5 | 150.0 | 10 | 1238 | 2250 |
|  | 40002 | 112.5 | 150.0 | 13 | 1688 | 2925 |
|  | 50001 | 112.5 | 112.5 | 7 | 788 | 1575 |
|  | N = 6 | 112.5 | 131.3 ± 20.5 | 9.7 ± 2.8 | 1181.3 ± 425.4 | 2175.0 ± 631.1 |
| r-hLH/Placebo | 10003 | 112.5 | 150.0 | 15 | 1988 | 3375 |
|  | 10005 | 112.5 | 112.5 | 2 | 225 | 450 |
|  | 30003 | 112.5 | 112.5 | 7 | 788 | 1575 |
|  | 40001 | 112.5 | 112.5 | 7 | 788 | 1575 |
|  | 50002 | 112.5 | 112.5 | 5 | 563 | 1125 |
|  | 60002 | 112.5 | 150.0 | 12 | 1538 | 2700 |
|  | N = 6 | 112.5 | 125.0 ± 19.4 | 8.0 ± 4.7 | 981.3 ± 654.9 | 1800.0 ± 1064.9 |
| Gonal-F/r-hLH | 10001 | 112.5 | 187.5 | 17 | 2363 | 3825 |
|  | 10006 | 112.5 | 112.5 | 3 | 338 | 675 |
|  | 20002 | 112.5 | 112.5 | 11 | 1238 | 2475 |
|  | 40003 | 112.5 | 112.5 | 7 | 788 | 1575 |
|  | 40004 | 112.5 | 112.5 | 7 | 788 | 1575 |
|  | 50003 | 112.5 | 112.5 | 6 | 675 | 1350 |
|  | 50004 | 112.5 | 150.0 | 11 | 1388 | 2475 |
|  | 60001 | 112.5 | 112.5 | 6 | 675 | 1350 |
|  | N = 8 | 112.5 | 126 ± 27.9 | 8.5 ± 4.3 | 1031.3 ± 632.0 | 1912.5 ± 977.1 |

| | | Blinded Phase | | |
|---|---|---|---|---|
| Treatment Group | Patient Id | Number of Days | Cumulative FSH Dose | Cumulative LH Dose | hCG Received |
| Gonal-F/Placebo | 10002 | 2 | 225 | | No |
|  | 10004 | 3 | 450 | | No |
|  | 20001 | 3 | 338 | | No |
|  | 30002 | 1 | 150 | | Yes |
|  | 40002 | 2 | 300 | | Yes |
|  | 50001 | 5 | 563 | | Yes |
|  | N = 6 | 2.7 ± 1.4 | 337.5 ± 150.0 | | 3 Yes/3 No |
| r-hLH/Placebo | 10003 | 3 | | 675 | No |
|  | 10005 | 5 | | 1125 | No |
|  | 30003 | 7 | | 1575 | No |
|  | 40001 | 5 | | 1125 | Yes |
|  | 50002 | 7 | | 1575 | No |
|  | 60002 | 4 | | 900 | Yes |
|  | N = 6 | 5.2 ± 1.6 | | 1162.5 ± 360.5 | 2 Yes/4 No |
| Gonal-F/r-hLH | 10001 | 3 | 563 | 675 | Yes |
|  | 10006 | 2 | 225 | 450 | No |
|  | 20002 | 1 | 113 | 225 | Yes |
|  | 40003 | 3 | 338 | 675 | Yes |
|  | 40004 | 2 | 225 | 450 | Yes |
|  | 50003 | 7 | 788 | 1575 | No |
|  | 50004 | 3 | 450 | 675 | Yes |
|  | 60001 | 2 | 225 | 450 | No |
|  | N = 8 | 2.9 ± 1.8 | 365.6 ± 223.0 | 646.9 ± 406.7 | 5 Yes/3 No |

TABLE 7

Summary Data on Number and Size of Follicles and hCG Cancellation

| | | Last US | | | | |
|---|---|---|---|---|---|---|
| Treatment Group | Patient Id | Number of Follicles >= 10 mm on T1 | Number of Follicles >= 11 mm | Number of Follicles >= 14 mm | hCG Received | Reason/Comment |
| Gonal-F/Placebo | 10002 | 1 | 5 | 1 | No | possible risk of multiple pregnancy |
|  | 10004 | 2 | 4 | 2 | No | 1 follicle 18 mm plus 3 > 11 mm; not within protocol |
|  | 20001 | 1 | 4 | 3 | No | multiple follicles |
|  | 30002 | 4 | 5 | 4 | Yes | |
|  | 40002 | 1 | 3 | 2 | Yes | |
|  | 50001 | 2 | 4 | 4 | Yes | |
|  | N = 6 | 1.83 ± 1.17 | 4.17 ± 0.75 *p = 0.5008 | 2.67 ± 1.21 *p = 0.4071 | 3 Yes/3 No | |
| r-hLH/Placebo | 10003 | 1 | 0 | 0 | No | regression of follicles |
|  | 10005 | 1 | 1 | 0 | No | regression of follicles |
|  | 30003 | 2 | 0 | 0 | No | failure of treatment |
|  | 40001 | 2 | 3 | 2 | Yes | |
|  | 50002 | 2 | 4 | 0 | No | failure of treatment |

TABLE 7-continued

Summary Data on Number and Size of Follicles and hCG Cancellation

| Treatment Group | Patient Id | Number of Follicles >= 10 mm on T1 | Last US Number of Follicles >= 11 mm | Number of Follicles >= 14 mm | hCG Received | Reason/Comment |
|---|---|---|---|---|---|---|
|  | 60002 | 1 | 1 | 1 | Yes |  |
|  | N = 6 | 1.50 ± 0.55 | 1.50 ± 1.64 | 0.50 ± 0.84 | 2 Yes/4 No |  |
|  |  |  | **p = 0.0171 | **p = 0.0162 |  |  |
| Gonal-F/r-hLH | 10001 | 1 | 4 | 2 | Yes |  |
|  | 10006 | 1 | 13 | 1 | No | risk of OHSS |
|  | 20002 | 2 | 2 | 2 | Yes |  |
|  | $^P$40003 | 4 | 3 | 1 | Yes |  |
|  | $^P$40004 | 3 | 3 | 1 | Yes |  |
|  | 50003 | 2 | 0 | 0 | No | failure of treatment |
|  | 50004 | 1 | 4 | 1 | Yes |  |
|  | 60001 | 2 | 19 | 8 | No | risk of OHSS |
|  | N = 8 | 2.00 ± 1.07 | 6.00 ± 6.50 | 2.00 ± 2.51 | 5 Yes/3 No |  |
|  |  |  | *p = 0.0032 | *p = 0.0412 |  |  | p values adjusted for BMI: contrast p-value with the previous treatment group
*Gonal-F/r-hLH vs. Gonal-F/Placebo
**Gonal-F/Placebo vs. r-hLH/Placebo
***r-ILH/Placebo vs. Gonal-F/r-hLH
$^P$pregnant patient

TABLE 8

Number of Patients with 0, 1, 2, 3, or >3 Follicles on the Day of hCG or on the Last Day of Treatment if No hCG was Administered

| Variable | Number of Follicles | Treatment Randomised | | | | | | Contrast** | p-values | | | |
|---|---|---|---|---|---|---|---|---|---|---|---|---|
|  |  | Gonal-F Placebo | | r-LH Placebo | | Gonal-F r-LH | | | One-sided | | Two-sided | |
|  |  | N | % | N | % | N | % |  | Asymptotic | Exact | Asymptotic | Exact |
| Follicles >= 11 mm | 0 foll. >= 11 mm | 0 | 0.0% | 2 | 33.3% | 1 | 12.5% | Gonal-F/Placebo vs r-hLH/placebo | 0.0057 | 0.0141 | 0.0115 | 0.0281 |
|  | 1 foll. >= 11 mm | 0 | 0.0% | 2 | 33.3% | 0 | 0.0% | Gonal-F/Placebo vs Gonal-F/r-hLH | 0.0820 | 0.1538 | 0.1641 | 0.2887 |
|  | 2 foll. >= 11 mm | 0 | 0.0% | 0 | 0.0% | 1 | 12.5% | r-hLH/Placebo vs Gonal-F/r-hLH | 0.0399 | 0.0653 | 0.0799 | 0.1016 |
|  | 3 foll. >= 11 mm | 1 | 16.7% | 1 | 16.7% | 2 | 25.0% | Overall comparison | 0.2051 | 0.2184 | 0.4101 | 0.4325 |
|  | >3 foll. >= 11 mm | 5 | 83.3% | 1 | 16.7% | 4 | 50.0% |  |  |  |  |  |
|  | All | 6 | 100.0% | 6 | 100.0% | 8 | 100.0% |  |  |  |  |  |
| Follicles >= 14 mm | 0 foll. >= 14 mm | 0 | 0.0% | 4 | 66.7% | 1 | 12.5% | Gonal-F/Placebo vs r-hLH/placebo | 0.0046 | 0.0076 | 0.0092 | 0.0152 |
|  | 1 foll. >= 14 mm | 1 | 16.7% | 1 | 16.7% | 4 | 50.0% | Gonal-F/Placebo vs Gonal-F/r-hLH | 0.0424 | 0.0766 | 0.0848 | 0.1485 |
|  | 2 foll. >= 14 mm | 2 | 33.3% | 1 | 16.7% | 2 | 25.0% | r-hLH/Placebo vs Gonal-F/r-hLH | 0.0461 | 0.0766 | 0.0922 | 0.1575 |
|  | 3 foll. >= 14 mm | 1 | 16.7% | 0 | 0.0% | 0 | 0.0% | Overall comparison | 0.1330 | 0.1377 | 0.2660 | 0.2769 |
|  | >3 foll. >= 14 mm | 2 | 33.3% | 0 | 0.0% | 1 | 12.5% |  |  |  |  |  |
|  | All | 6 | 100.0% | 6 | 100.0% | 8 | 100.0% |  |  |  |  |  |

Contrast**
Overall Comparison: Jockheere-Terpstra test
Pairwise Comparison: Cochran-Arimitag test for trend.

TABLE 9

Descriptive Statistics of Hormone Levels
Measured at T1 and on the Day of hCG or on the Last Day of Treatment if No hCG was Administered

| Variable | Treatment | T1 (first day of stimulation) | | | | | Day of hCG or last day of treatment if no hCG was administered | | | | |
|---|---|---|---|---|---|---|---|---|---|---|---|
|  |  | n | Mean | SD | SEM | Median | Range | n | Mean | SD | SEM | Median | Range |
| FSH (IU/L) | Gonal-F/Placebo | 6 | 8.58 | 3.19 | 1.30 | 8.05 | (5-14) | 5 | 8.52 | 3.13 | 1.40 | 7.00 | (5-12) |
|  | r-hLH/Placebo | 6 | 12.37 | 6.73 | 2.75 | 9.85 | (9-26) | 6 | 3.33 | 2.13 | 0.87 | 3.00 | (1-6) |
|  | Gonal-F/r-hLH | 8 | 9.68 | 3.44 | 1.22 | 10.15 | (4-15) | 8 | 9.03 | 2.66 | 0.94 | 9.55 | (4-13) |
|  | All | 20 | 10.16 | 4.62 | 1.03 | 9.75 | (4-26) | 19 | 7.09 | 3.62 | 0.83 | 7.00 | (1-13) |

TABLE 9-continued

Descriptive Statistics of Hormone Levels
Measured at T1 and on the Day of hCG or on the Last Day of Treatment if No hCG was Administered

| Variable | Treatment | T1 (first day of stimulation) | | | | | | Day of hCG or last day of treatment if no hCG was administered | | | | | |
|---|---|---|---|---|---|---|---|---|---|---|---|---|---|
| | | n | Mean | SD | SEM | Median | Range | n | Mean | SD | SEM | Median | Range |
| LH (IU/L) | Gonal-F/Placebo | 6 | 1.08 | 0.16 | 0.07 | 1.00 | (1-1) | 5 | 1.00 | 0.00 | 0.00 | 1.00 | (1-1) |
| | r-hLH/Placebo | 6 | 1.30 | 0.60 | 0.24 | 1.00 | (1-3) | 6 | 1.88 | 1.56 | 0.64 | 1.25 | (1-5) |
| | Gonal-F/r-hLH | 8 | 1.58 | 0.87 | 0.31 | 1.10 | (1-3) | 8 | 1.56 | 0.71 | 0.25 | 1.35 | (1-3) |
| | All | 20 | 1.35 | 0.65 | 0.15 | 1.00 | (1-3) | 19 | 1.52 | 1.00 | 0.23 | 1.00 | (1-5) |
| E2 (pmol/L) | Gonal-F/Placebo | 6 | 691.50 | 737.24 | 300.98 | 474.5 | (160-2171) | 5 | 725.80 | 989.66 | 442.59 | 302.00 | (163-2483) |
| | r-hLH/Placebo | 6 | 669.33 | 483.03 | 197.20 | 630.00 | (129-1311) | 6 | 116.33 | 102.12 | 41.69 | 100.00 | (33-316) |
| | Gonal-F/r-hLH | 8 | 1416.50 | 1666.01 | 589.02 | 650.00 | (187-4885) | 7 | 3452.86 | 3843.18 | 1452.59 | 1537.00 | (251-11257) |
| | All | 20 | 974.85 | 1167.89 | 261.15 | 474.50 | (129-4885) | 18 | 1583.17 | 2803.84 | 660.87 | 309.00 | (33-11257) |
| P4 (nmol/L) | Gonal-F/Placebo | 6 | 1.4 | 0.6 | 0.2 | 1.1 | (1-2) | 5 | 1.6 | 0.8 | 0.4 | 1.3 | (1-3) |
| | r-hLH/Placebo | 6 | 2.1 | 1.1 | 0.4 | 1.6 | (1-4) | 6 | 1.9 | 1.5 | 0.6 | 1.2 | (1-5) |
| | Gonal-F/r-hLH | 8 | 2.3 | 1.3 | 0.5 | 2.0 | (1-5) | 7 | 22.9 | 53.0 | 20.0 | 2.8 | (2-143) |
| | All | 20 | 2.0 | 1.1 | 0.2 | 1.6 | (1-5) | 18 | 10.0 | 33.2 | 7.8 | 1.9 | (1-143) |
| Andro-stenedione (nmol/L) | Gonal-F/Placebo | 6 | 4.87 | 2.55 | 1.04 | 3.65 | (3-10) | 4 | 4.08 | 2.35 | 1.18 | 3.20 | (2-8) |
| | r-hLH/Placebo | 6 | 5.93 | 2.50 | 1.02 | 5.65 | (3-9) | 6 | 5.63 | 2.37 | 0.97 | 5.15 | (3-10) |
| | Gonal-F/r-hLH | 8 | 7.71 | 3.78 | 1.34 | 7.30 | (3-14) | 8 | 10.58 | 6.19 | 2.19 | 10.80 | (3-22) |
| | All | 20 | 6.33 | 3.19 | 0.71 | 5.85 | (3-14) | 18 | 7.48 | 5.18 | 1.22 | 5.90 | (2-22) |

The invention claimed is:

1. A method for inducing paucifolliculogenesis or unifolliculogenesis in WHO group II anovulatory women, comprising administering to WHO group II anovulatory women as an active agent LH at a daily dose in the range of 100 to 1500 IU, or an equivalent daily dose of hCG, starting in the mid- to late-follicular phase to induce paucifolliculogenesis or unifolliculogenesis, wherein the administration is to be started when there is at least one follicle having a mean diameter in a range of 11 to 14 mm and wherein the administration of FSH has been discontinued.

2. The method of claim 1, comprising administering to WHO group II anovulatory women as an active agent hCG at a daily dose equivalent to a daily dose of LH in the range of 100 to 1500 IU, starting in the mid- to late-follicular phase to induce paucifolliculogenesis or unifolliculogenesis, wherein the equivalent dose of hCG is calculated as 1 IU of hCG being equivalent to 5-7 IU of LH.

* * * * *